United States Patent
Mendonsa et al.

(10) Patent No.: US 11,774,366 B2
(45) Date of Patent: Oct. 3, 2023

(54) SEQUENCING NUCLEIC ACIDS VIA SURFACE ENHANCED RAMAN SPECTROSCOPY

(71) Applicant: Seagate Technology LLC, Fremont, CA (US)

(72) Inventors: Gemma Mendonsa, Minneapolis, MN (US); Eric K. Wadleigh, Shakopee, MN (US); Vivek Krishnamurthy, Normandale, MN (US); Riyan A. Mendonsa, Minneapolis, MN (US); Martin G. Blaber, Normandale, MN (US); Krishnan Subramanian, Shakopee, MN (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 523 days.

(21) Appl. No.: 16/986,108

(22) Filed: Aug. 5, 2020

(65) Prior Publication Data
US 2021/0148828 A1 May 20, 2021

Related U.S. Application Data

(60) Provisional application No. 62/938,264, filed on Nov. 20, 2019.

(51) Int. Cl.
| | |
|---|---|
| *C12Q 1/6869* | (2018.01) |
| *G01N 21/65* | (2006.01) |
| *C12N 9/12* | (2006.01) |
| *G01N 27/447* | (2006.01) |
| *B82Y 30/00* | (2011.01) |

(52) U.S. Cl.
CPC ......... *G01N 21/658* (2013.01); *C12N 9/1252* (2013.01); *C12Q 1/6869* (2013.01); *G01N 27/44786* (2013.01); *B82Y 30/00* (2013.01)

(58) Field of Classification Search
CPC ............ B82Y 30/00; G01N 27/44786; G01N 21/658; C12Q 1/6869; C12N 9/1252
See application file for complete search history.

(56) References Cited

U.S. PATENT DOCUMENTS

| | | | |
|---|---|---|---|
| 5,306,403 A | 4/1994 | Vo-Dinh | |
| 6,043,034 A | 3/2000 | Takama et al. | |
| 7,364,851 B2 | 4/2008 | Berlin et al. | |
| 7,465,578 B2 | 12/2008 | Berlin et al. | |
| 9,624,539 B2 | 4/2017 | Ju et al. | |
| 9,689,743 B2 | 6/2017 | Liu et al. | |
| 9,733,125 B2 | 8/2017 | Liu et al. | |
| 2006/0068440 A1* | 3/2006 | Chan | C12Q 1/6869 435/6.1 |
| 2007/0105132 A1 | 5/2007 | Berlin et al. | |

(Continued)

OTHER PUBLICATIONS

T. Vo-Dinh, "Surface-Enhanced Raman Gene Probes", 1994 (Year: 1994).*

*Primary Examiner* — Maurice C Smith
(74) *Attorney, Agent, or Firm* — HOLZER PATEL DRENNAN

(57) ABSTRACT

A Surface-Enhanced Raman Spectroscopy (SERS) device to perform accurate label-free long-read DNA sequencing. A Raman sensor has a hot spot defined by plasmonic nanostructures and excited by at least one laser. An immobilized DNA polymerase can be used to pull a DNA template strand to be sequenced through the hot spot.

20 Claims, 11 Drawing Sheets

(56) References Cited

U.S. PATENT DOCUMENTS

| | | | | |
|---|---|---|---|---|
| 2010/0267158 A1* | 10/2010 | Chou | ................... | B82Y 35/00 216/13 |
| 2014/0204372 A1* | 7/2014 | Pang | ................... | G01N 21/658 356/244 |
| 2014/0367259 A1* | 12/2014 | Frayling | .............. | G01N 21/658 204/452 |

* cited by examiner

SEQUENCING NUCLEIC ACIDS VIA SURFACE ENHANCED RAMAN SPECTROSCOPY

CROSS-REFERENCE

This application claims priority to U.S. provisional application No. 62/938,264 filed Nov. 20, 2019 and titled "Sequencing Nucleic Acids via Surface Enhanced Raman Spectroscopy," the entire disclosure of which is incorporated herein by reference for all purposes.

SUMMARY

This disclosure is directed to Surface-Enhanced Raman Spectroscopy (SERS) sensors or devices, and methods of using, to perform accurate, tag-free or label-free, long-read DNA sequencing. More specifically, this disclosure is directed to devices and methods of utilizing SERS to identify individual nucleotides.

To identify the individual nucleotides, a DNA template strand passes through a Raman hot spot generated by laser excitation and enhanced by resonance of plasmonic (e.g., gold) nanostructures.

This disclosure provides, in one particular implementation, a method of sequencing a DNA strand. The method includes passing the DNA strand through a nanochannel hot spot of a Raman sensor bounded by plasmonic nanostructures and excited by at least one laser, identifying the nucleotides of a first section of the DNA strand present in the channel at a first period in time by a Raman signature, and identifying the nucleotides of a second section of the DNA strand present in the channel at a second period in time by a second Raman signature, and comparing the identified nucleotides of the first section to the identified nucleotides of the second section to identify a change.

In another particular implementation, another method of sequencing a DNA strand is provided. The method includes passing the DNA strand through a nanochannel hot spot of a Raman sensor bounded by plasmonic nanostructures and excited by at least one laser, identifying a Raman signature of at least one nucleotide of a first section of the DNA strand present in the channel at a first period in time, and identifying a second Raman signature of at least one nucleotide of a second section of the DNA strand present in the channel at a second period, comparing the Raman signature of the first section to the second Raman signature of the second section to identify a change in the Raman signature, and correlating the change in the Raman signature to a single nucleotide.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. These and various other features and advantages will be apparent from a reading of the following detailed description.

BRIEF DESCRIPTION OF THE DRAWING

The described technology is best understood from the following Detailed Description describing various implementations read in connection with the accompanying drawing.

DETAILED DESCRIPTION

Figure 1:
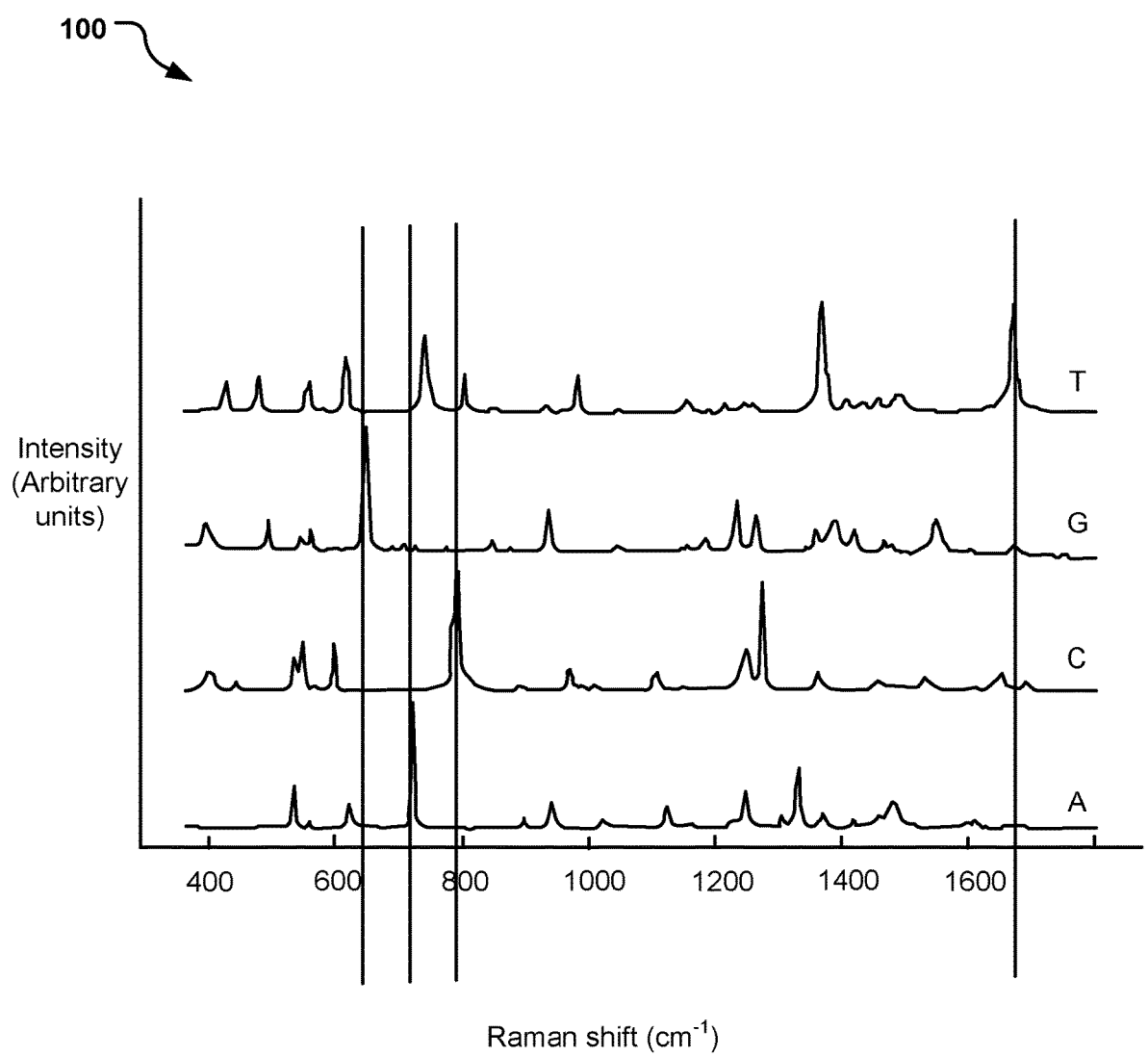
FIG. 1 is a graphical representation of Raman spectra for nucleotides.

Current DNA sequencing methods face limitations in sequence read length, sensitivity, and run time. A higher sensitivity or signal/noise ratio would improve sequencing accuracy in long reads. The length of the DNA strand to be sequenced is limited by the use of labels; most labels do not give a strong signal and require multiple molecules to generate signals simultaneously. As the sequence length increases, the individual molecular signals fall out of sync, limiting the length of accurate sequence. Run times are long due to the need to pause after each base incorporation to obtain an optical signal and/or remove tags; this could be improved with the use of real-time sequencing via a label-free system.

In the following description, reference is made to the accompanying drawing that forms a part hereof and in which is shown by way of illustration at least one specific implementation. The following description provides additional specific implementations. It is to be understood that other implementations are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples, including the figures, provided below. In some instances, a reference numeral may have an associated sub-label consisting of a lower-case letter to denote one of multiple similar components. When reference is made to a reference numeral without specification of a sub-label, the reference is intended to refer to all such multiple similar components.

Surface Enhanced Raman Spectroscopy (SERS) is an ultrasensitive optical detection method that can be used to identify molecules based on their unique Raman scattering spectra. DNA has four nucleotides (adenine (A), cytosine (C), guanine (G), and thymine (T)) each which emits Raman-scattered photons with unique frequencies when excited by a laser. FIG. 1 shows a graph 100 of the Raman spectra of nucleotides adenine (A), cytosine (C), guanine (G), and thymine (T) at an excitation wavelength of 514.5 nm. Example peaks that may be used for nucleotide identification are identified in FIG. 1: 721 cm$^{-1}$ for A, 776 cm$^{-1}$ for C, 643 cm$^{-1}$ for G, and 1680 cm$^{-1}$ for T.

The nucleotides (A, C, G, T) in a DNA strand are only 0.34 nm apart; because of this small spacing, it is not feasible to observe and identify only one nucleotide at a time using conventional SERS. Attempts have been made, however, to use SERS to identify single nucleotides when labeled with a tag or other identifier that is more sensitive to SERS.

The proposed solution described below enables highly accurate sequencing through use of SERS to identify individual, unlabeled or untagged, nucleotides. The proposed method is label-free, enabling fast sequencing and long read lengths. Current sequencing methods are unable to provide all three qualities of accuracy, long read length capability, and speed. SERS can be used as described below to provide these three qualities together in an elegant solution.

In this disclosure, a Raman sensor or device is described that has a Raman "hot spot" channel formed by laser excitation and enhanced by resonance of focusing plasmonic (e.g., gold, silver) nanostructures. An unlabeled or untagged DNA template strand is drawn or fed through the hot spot channel. As the DNA template strand moves through the hot spot, Raman spectra for the individual nucleotides are measured. In some implementations, the Raman spectra for a first group of nucleotides present in the hot spot channel is measured at a first point in time, and the Raman spectra for a second group of nucleotides present in the hot spot channel is measured at a second point in time subsequent to the first point in time. The two Raman spectra are compared to determine what nucleotide(s) left the hot spot and what nucleotide(s) entered the hot spot.

In some implementations, the device includes a DNA polymerase, which replicates the template strand being sequenced. The replication action by the polymerase pulls the template strand through the hot spot channel. In some implementations, a secondary force, e.g., an electric force or voltage differential, is additionally or alternatively used to aid the passage of the strand through the hot spot channel between the nanostructures.

The sensor may be considered an "on chip" system.

Figure 2:
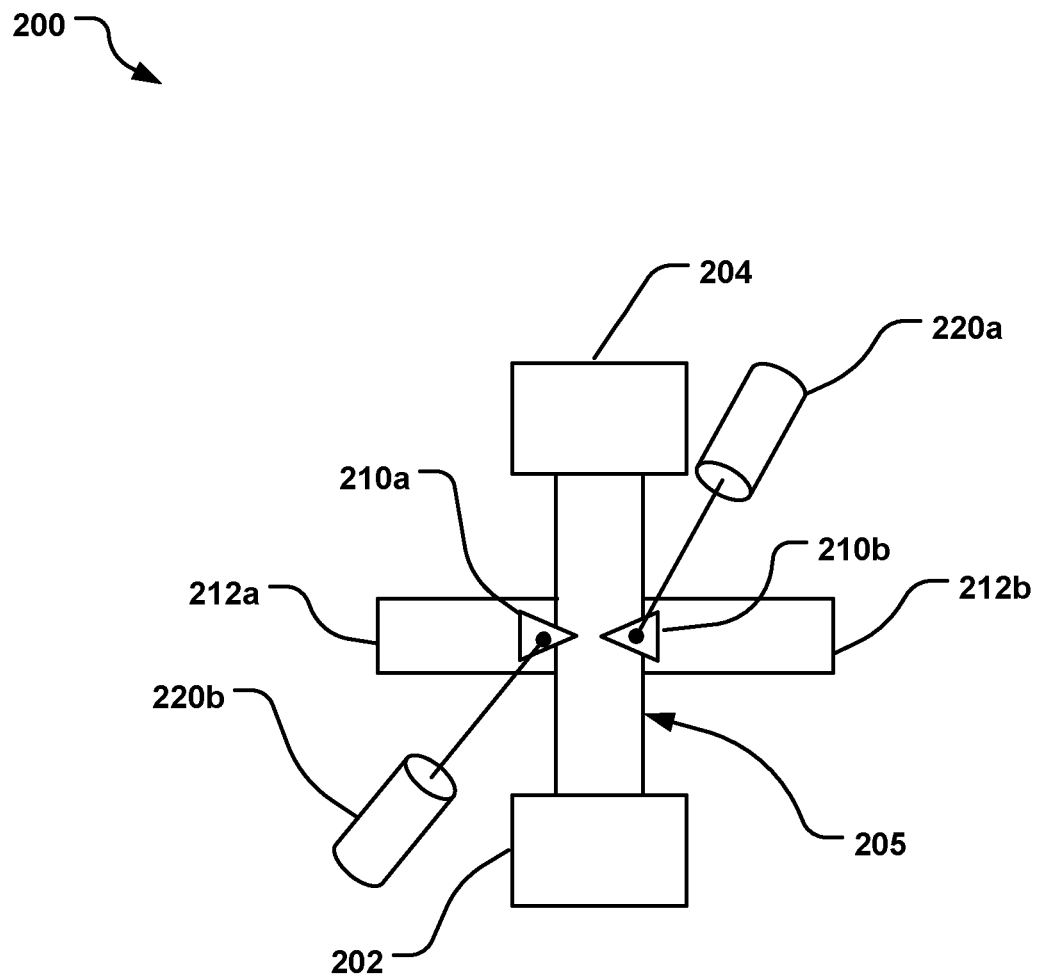
FIG. 2 is a schematic diagram of a Raman sensor set-up.

FIG. 2 generally illustrates a SERS sensor 200 for sequencing a DNA template strand. The sensor 200 has a sample loading chamber 202 and a secondary or sample receiving chamber 204. Connecting the two chambers 202, 204 is a nanochannel 205. Although the nanochannel 205 is shown having a length, the nanochannel 205 may merely be an orifice between the two chambers 202, 204, a region defined by a plane separating the two chambers 202, 204, or the nanochannel 205 may be a channel bounded on some or all sides by physical walls. Suitable lengths and widths of the nanochannel 205 are in a wide range. In some implementations, the width of the nanochannel 205 is in the range of 1 nm to 100 nm, or 1 nm to 50 nm, although nanochannels less than 1 nm are known and are suitable. In some implementations, the width of the nanochannel is 0.2 nm to 2 nm.

A pair of nanostructures 210a, 210b are located on opposites sides of the nanochannel 205, operably connected to a pair of waveguides 212a, 212b. The nanostructures 210 focus the Raman signal to a small region (e.g., 1-10 nm wide) in the nanochannel 205. Typically, the tapered or pointed ends of the nanostructures 210 are spaced a distance no greater than the width of the nanochannel 205; in other words, the distance between the tips of the nanostructures 210 could be less than or the same as the nanochannel 205 width. In some implementations, the tips of the nanostructures 210 have a distance of 0.2 nm to 5 nm therebetween.

Figure 3A:
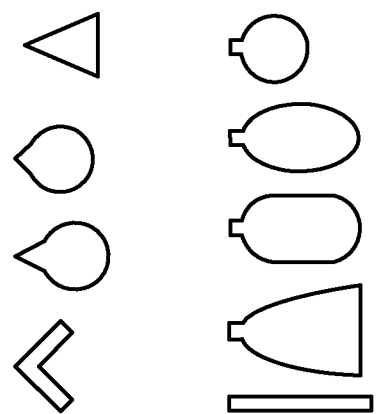
FIG. 3A shows various alternate designs of nanostructures.

The nanostructures 210 may be any of a variety of shapes, such as triangular (as in FIG. 2), lollipop, other pointed surface designs, etc. Two oppositely positioned triangular nanostructures resemble a bow tie, and two oppositely positioned lollipop nanostructures resemble a dumbbell. The nanostructures 210 may be two-dimensional or three-dimensional. Tapered or pointed nanostructures 210 are particularly useful for focusing the signal. FIG. 3A illustrates various alternate designs of nanostructures.

The shape and size of the nanostructures is chosen so that, in combination with the dimensions of the nanochannel, the mode of light in the waveguide and the wavelength of light, a resonance occurs that creates electromagnetic hot spots in the gap between the nanostructures. Typically, the nanostructures are in the range of 100 nm to 2000 nm, in their largest dimension.

Figure 3B:
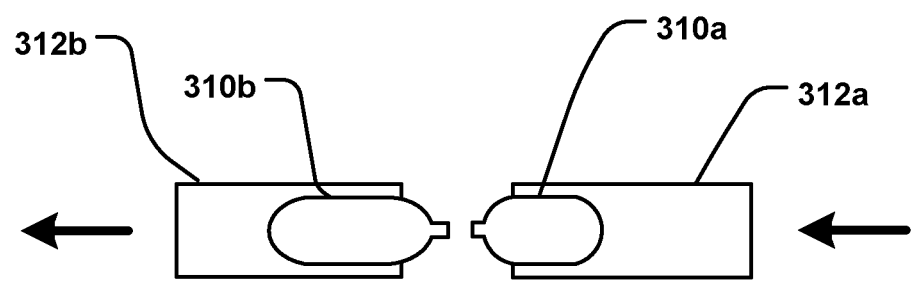
FIG. 3B is a schematic diagram of a Raman sensor set-up with an example light input arrangement.

Efficiency of the nanostructures and the sensor can be improved by increasing the size of the output nanostructure, so that it is better optimized to convert the lower energy plasmon into a photon and couple it to the waveguide. FIG. 3B illustrates a portion of a sensor having input nanostructure 310a and input waveguide 312a and output nanostructure 310b and output waveguide 312b, with the direction of light indicated. Alternately, the output waveguide dimension can be optimized to more efficiently carry the lower energy red-shifted light.

The nanostructures 210 are plasmonic nanostructures and may be made of gold, silver, platinum or another plasmonic material, or a combination of plasmonic and other materials.

In some implementations, more than one pair of nanostructures 210 is present. For example, three nanostructures 210 may be arranged equidistant around the nanochannel 205, at 120 degree angles to each other; as another example, four nanostructures 210 may be arranged equidistant around the nanochannel 205, at 90 degree angles to each other. In other implementations, multiple nanostructures 210 are not equidistantly spaced. Multiple nanostructures 210 may be in the same plane or may not.

Figure 4A:
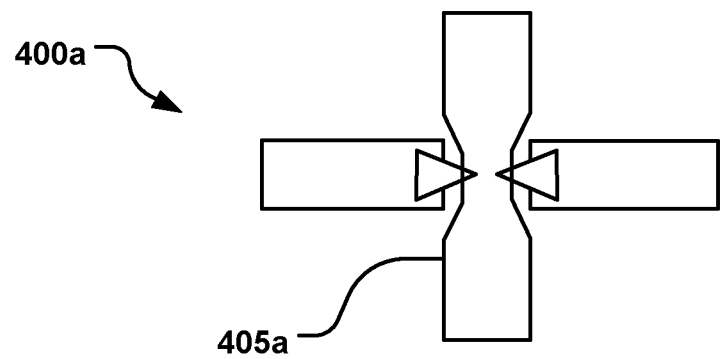
FIGS. 4A, 4B and 4C are schematic diagrams of Raman sensor set-ups having tapered nanochannels.
Figure 4B:
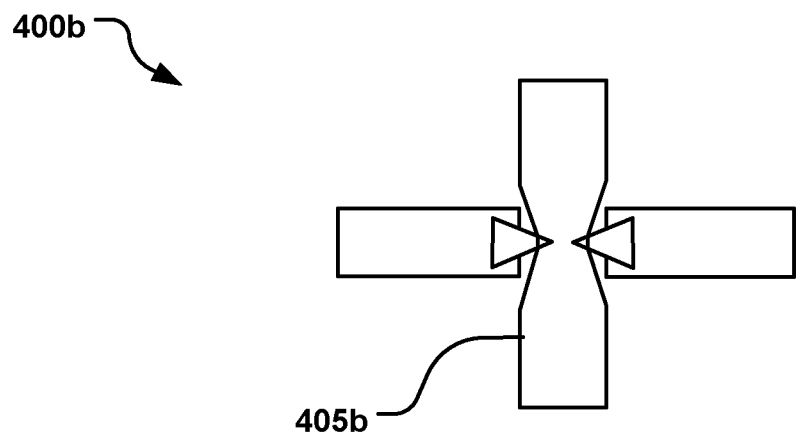
Figure 4C:
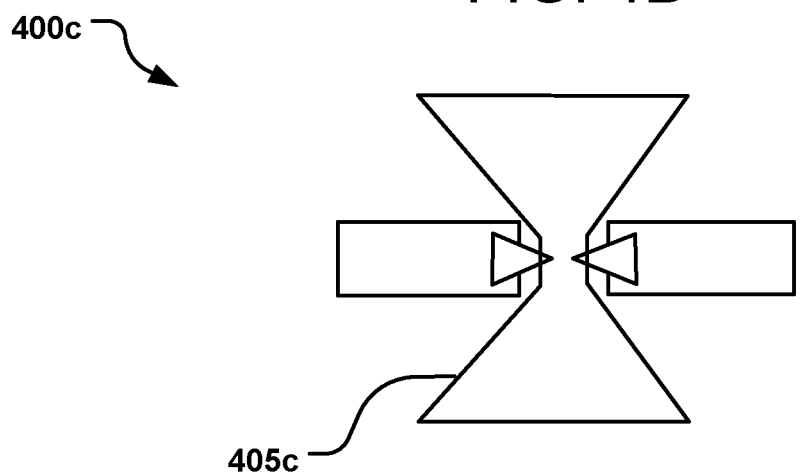

Additional nanostructures or other structures may be added upstream of the plasmonic nanostructures 210 to create a longer nanochannel 205 to linearize the DNA strand prior to it reaching the plasmonic nanostructures 210. In some implementations, the nanochannel may be tapered or otherwise shaped to facilitate the passing of the DNA strand therethrough. FIG. 4A shows a device 400a having a first tapered nanochannel 405a, FIG. 4B shows a device 400b having another tapered nanochannel 405b, and FIG. 4C shows a device 400c having a drastically tapered nanochannel 405c.

At least one laser 220 is focused on at least one of the nanostructures 210, in the region of the nanochannel 205; FIG. 2 shows two lasers 220a, 220b, each focused on a nanostructure 210. In some implementations, multiple lasers 220 are used for each pair of nanostructures; thus, for two pairs (four) nanostructures, at least four lasers are used.

The laser(s) 220 are directed at the nanostructures 210 and/or the gap between them, to generate plasmons across the nanostructures 210 and create a Raman hot spot in the nanochannel 205. The laser beam(s) have a much greater diameter or area of impact than the end of the nanostructures 210. Any material (e.g., nucleotides) in the hot spot will be excited by the laser and emit Raman-scattered photons.

The laser(s) 220 may be, e.g., a solid state laser, a gas (e.g., xenon) laser, a liquid laser, etc., or any similar light source operating at, e.g., 600 nm, 800 nm, 1064 nm wavelengths. If multiple lasers 220 are present, they may have the same or different wavelengths; if different, the wavelengths will differ by at least a few 100 nm. The laser(s) 220 may be a tunable laser, a continuous laser, or a pulsed laser. The laser(s) 220 may be polarized. Lasers 220 having a wattage of 1 mW to 100 mW are suitable. In one particular implementation, the laser is an edge-emitting semiconductor laser.

A secondary light source (e.g., visible light or other) may be used to stimulate photon emission. This secondary source may be, e.g., a single fixed laser, multiple lasers, or a tunable laser or a pulsed laser.

Multiple lasers 220 may be positioned parallel to or perpendicular to the nanostructures and may be on the same plane or a separate plane. As an example, three planar lasers 220 may be arranged equidistant around the nanochannel 205, at 120 degree angles to each other; as another example, four lasers 220 may be arranged equidistant around the nanochannel 205, at 90 degree angles to each other. In other implementations, multiple planar lasers 220 are not equidistantly spaced. Although multiple lasers 220 may not be planar, the focal point of all the lasers 220 is in the same region to form the "hot spot."

Figure 5A:
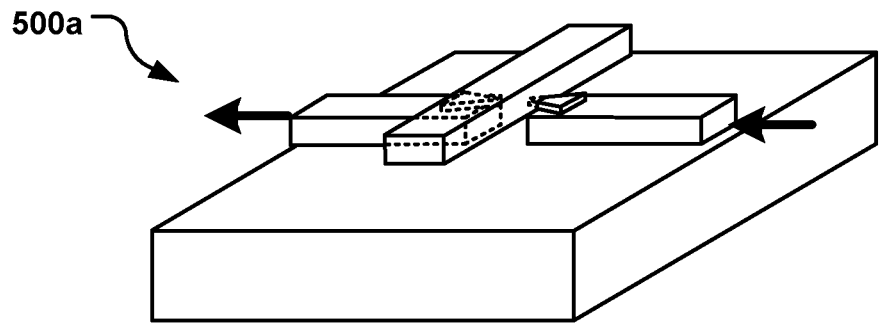
FIGS. 5A, 5B and 5C are schematic diagram of various laser set-ups for Raman sensors.
Figure 5B:
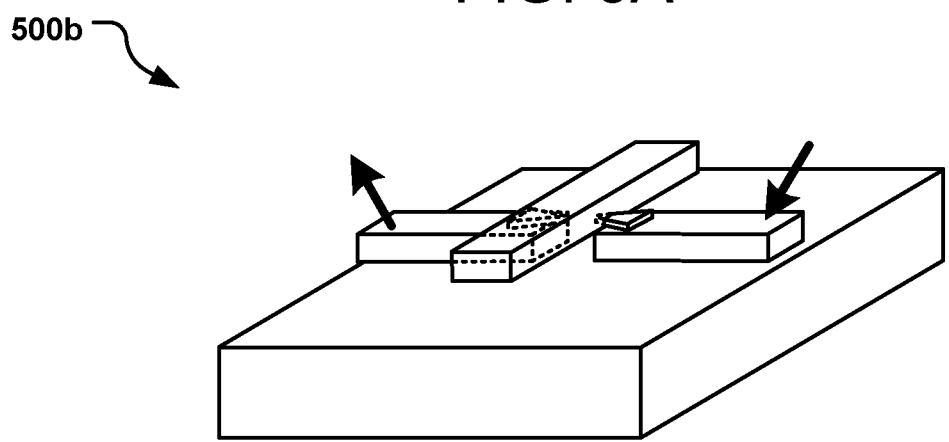
Figure 5C:
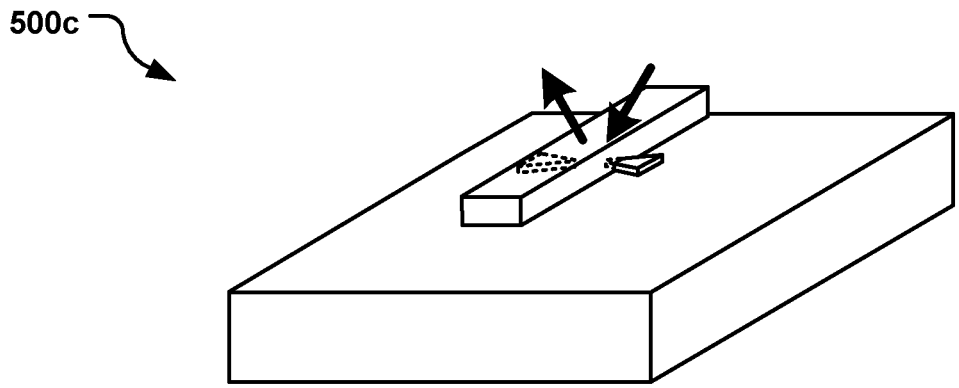

In some implementations, as shown in FIG. 2, waveguides 212 may be used to direct the laser beam(s) to the nanostructures 210. FIGS. 5A, 5B and 5C show three implementations of utilizing waveguides to direct light to the nanostructures.

In FIG. 5A, a laser positioned (e.g., glued) at the end of the waveguide, carefully aligned to the waveguide. A trench may be present in the substrate of the sensor (e.g., wafer) to receive the laser so that its output facet aligns with the waveguide. A coupler can be used to shrink the light from the output facet of the laser to the final size of the channel waveguide. If the mode of the laser does not correspond to the transducer, a mode converter may be used. The light in the waveguide can be either transverse magnetic (TM) or transverse electric (TE).

FIG. 5B shows use of an external laser, with the light from the external laser coupled to the channel waveguide. A grating coupler can be patterned at the same time that the waveguide is formed. A single external laser with a splitter can be used, rather than multiple lasers, for multiple waveguides, each with its own transducer.

In FIG. 5C, an external laser is used to directly illuminate the transducer, without utilizing a waveguide.

No matter the laser or other light source configuration, the resulting Raman photons or light scattered by the nucleotides (hence, the Raman spectra) are measured and the nucleotides identified. Stokes scattered photons, Anti-Stokes scattered photons, or both may be used for nucleotide identification. The Raman scattered photons may be collected and/or focused by mirrors or lenses to facilitate identification of the nucleotides, or the scattered light may be collected by a waveguide. Light may be detected and quantified by a photomultiplier tube, photodiode array, charge-coupled device, electron multiplied charge-coupled device, etc. The resulting Raman-scattered photons may be filtered such that only photons of specific frequencies are detected. Examples regarding filtering the Raman-scattered photons are provided below. In some implementations, optical resonator(s) may be present to increase the signal from the detected photons.

Returning to FIG. 2, the length of the Raman hot spot may be the entire length of the nanochannel 205 or may be less than the entire length of the nanochannel 205. The length of the hot spot is based on the focal points of the laser(s) 220 in relation to the nanostructures 210. The length of the hot spot may be, e.g., 1-10 nm long.

The SERS sensor 200 can be provided as a microfluidic lab-on-a-chip system, or, "on chip." Lab-on-a-chip is a common term for an integrated circuit ("chip") on which one or several laboratory functions or chemical reactions are done. The chip can be no more than a few square centimeters. Labs-on-a-chip handle extremely small fluid volumes (e.g., measured as e.g., microliters, nanoliters, or pico-liters) and are often called microfluidic systems. In digital microfluidics, the lab-on-a-chip has a hydrophobic "chip platform" on which fluid droplets (e.g., liquid droplets) can be manipulated by precisely controlled voltage application.

The chip may be formed from two or more detachable parts: one part containing the Raman detectors, the nanostructures 210 and the lasers 220, another part containing capillaries that form the chambers 202, 204 and nanochannel 205. Alternately, the nanostructures 210 could be in the second part with the nanochannel 205. Such constructions would enable the reuse of expensive electronic and photonic pieces and the disposal of the fluidic area. The platform may have a cover plate covering the fluidic area. By utilizing the physical structure of the platform, the fluid (DNA template strand sample) can be precisely moved across the platform, e.g., by the pulling by the DNA polymerase. In some implementations, the fluid can be moved across the platform by voltage or electric field applied to the platform, e.g., by a grid in the platform.

In use of the sensor 200, a DNA template strand, present in the sample loading chamber 202, is drawn or fed through the nanochannel 205 through the hot spot formed by the nanostructures 210 and the laser(s) 220. The laser(s) 220, focused on the nanostructures 210, enhance the Raman spectra or resonance obtained from the scattered photons, allowing each individual nucleotide to be identified by its Raman spectra.

The DNA template strand can be drawn through the nanochannel 205 from the sample loading chamber 202 to the secondary chamber 204 by a DNA polymerase. A DNA polymerase can pull the DNA template strand through the nanochannel 205 at a rate of about 70-75 nucleotides per second, or, about 14 milliseconds per nucleotide. This may change, however, dependent on, e.g., the type of DNA polymerase, the temperature of the sensor and/or the system.

Figure 6:
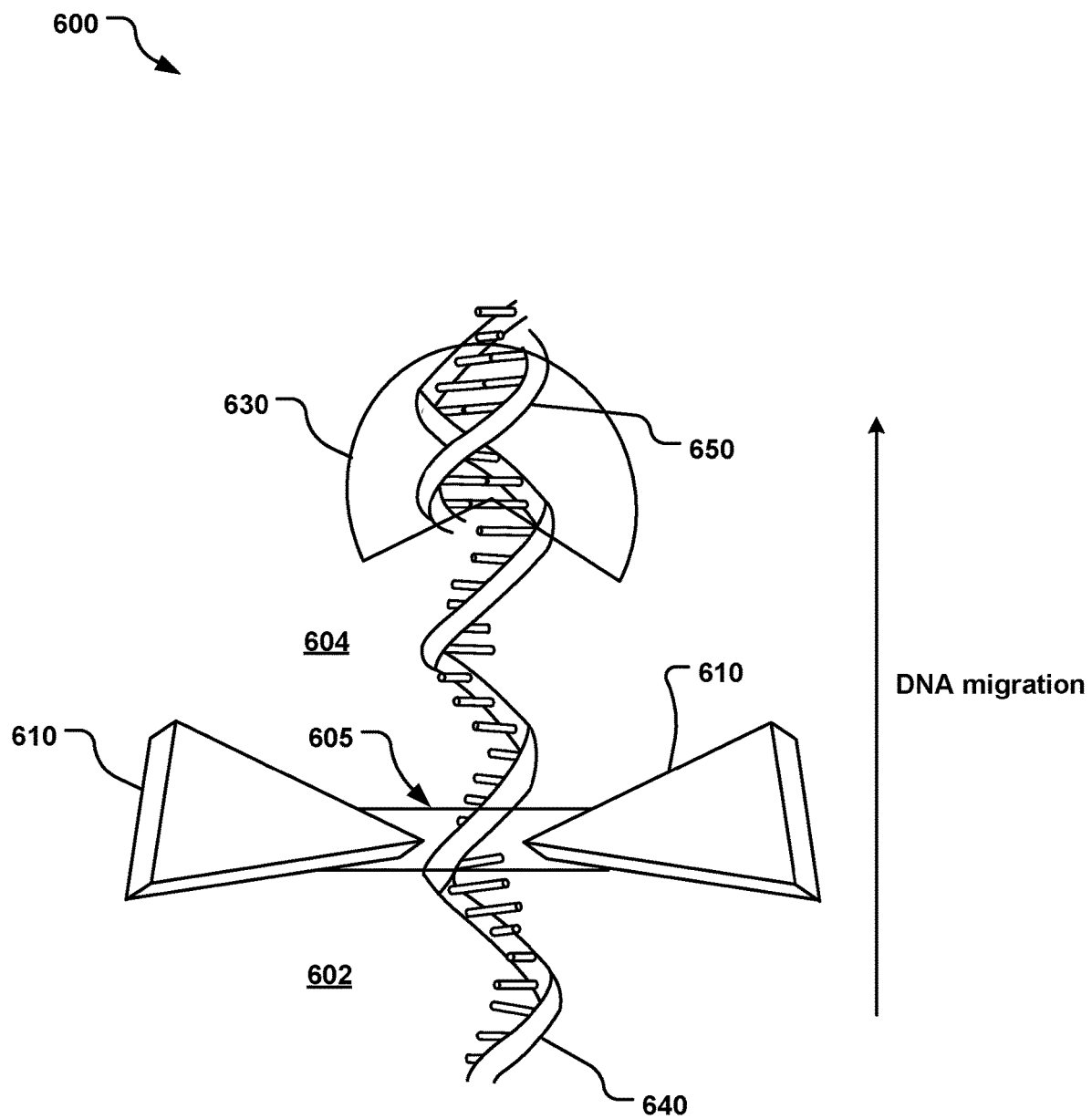
FIG. 6 is another schematic diagram of a Raman sensor set-up.

In FIG. 6, a SERS sensor 6 is schematically illustrated, almost in a cartoon manner. Only certain features of the sensor 600 are shown in FIG. 6; it is to be understood that the sensor 600 includes other features (e.g., laser(s)) as described in relation to FIG. 2.

The sensor 600 has a sample loading chamber 602, a secondary chamber 604, and a nanochannel hot spot 605 therebetween. This nanochannel hot spot 605 is generated by laser excitation and enhanced by resonance of metallic (e.g., gold) nanostructures 610. In some implementations, the nanostructures 610 define the distinction between the two chambers 602, 604. The sample loading chamber 602 is upstream of the nanochannel hot spot 605 and the secondary chamber 604 is downstream of the nanochannel hot spot 605.

A DNA polymerase 630 (illustrated as a Pac Man™ type shape) replicates a DNA template strand 640 to be sequenced. The DNA template strand 640 is not tagged, labeled, or in no other way are the nucleotides identified or distinguished from each other. The DNA polymerase 630 may be immobilized, e.g., on a surface of the secondary chamber 604 or otherwise downstream of the nanochannel hot spot 605. The replicated complementary strand 650 is shown proximate the DNA polymerase 630. The action of replicating the template strand 640, by the DNA polymerase 630, applies a tension or force on the strand 640 and pulls the strand through the Raman nanochannel hot spot 605. Each of the nucleotides, as it passes through the nanochannel hot spot 605, generates a unique Raman signal depending on its identity.

In use of the sensor 600, a carrier solution (containing the template DNA strand 640 to be sequenced) is added to the sample loading chamber 602. A solution containing free nucleotides A, C, G, and T is added to the secondary chamber 604. The template strand 640 may then be threaded through the nanochannel 605 between the nanostructures 610 using, e.g., an electric field or electrophoresis, or magnetophoresis. Once the template strand 640 has been threaded through the gap and has reached the secondary chamber 604, the template strand 640 encounters the immobilized DNA polymerase 630. The template strand 640 binds to the polymerase 630, which then creates a copy of the template strand 640 by incorporating the nucleotides from the solution one at a time into a growing complementary strand 650; see, e.g., FIG. 6, which shows the DNA polymerase 630 forming the complementary strand 650. At this point, any applied field can be removed.

The action of the DNA polymerase 630 on the template strand 640 pulls the remainder of the single stranded template strand 640 through the nanochannel hot spot 605. The migration of the template strand 640 through the sensor region (i.e., the hot spot 605) is smoothly controlled by the incorporation rate of the polymerase. As the template strand 640 is pulled through the nanochannel hot spot 605 from the sample loading chamber 602 into the secondary chamber 604, a portion of the strand 640 is in the Raman n hot spot 605. This portion of the strand in the nanochannel hot spot 605 will change as the strand 640 is pulled through.

Because the nucleotides are a fixed distance apart (i.e., 0.34 nm), a set number of nucleotides will be present in the nanochannel hot spot 605 at any given time, the number based on the length of the nanochannel hot spot 605. As the DNA polymerase 630 incorporates one nucleotide, it pulls the template strand 640 through the nanochannel hot spot 605 so that as one nucleotide leaves the nanochannel hot spot 605, one nucleotide enters the nanochannel hot spot 605. The new section of template strand 640 (and hence, the sequence) present in the nanochannel hot spot 605 will differ from the previous section (and hence, sequence) by one nucleotide; the one nucleotide that leaves the nanochannel hot spot 605 is replaced by the one entering the nanochannel hot spot 605. Although the nucleotides from the second group or set differ by only one from the first group or set of nucleotides, they are in a different order, shifted by one.

The nucleotides present in the nanochannel hot spot emit Raman-scattered photons, which can then be filtered and detected. Each of the nucleotides A, C, G, T emit Raman photons of specific frequencies (see, FIG. 1). The amplitude of the signal intensity at each selected frequency can be used to determine the quantity of each nucleotide present in the hot spot at any given time. The change in signal amplitude between the new sequence in the hot spot and the previous sequence in the hot spot can be used to determine which nucleotide left the hot spot and which nucleotide joined the hot spot.

Figure 7:
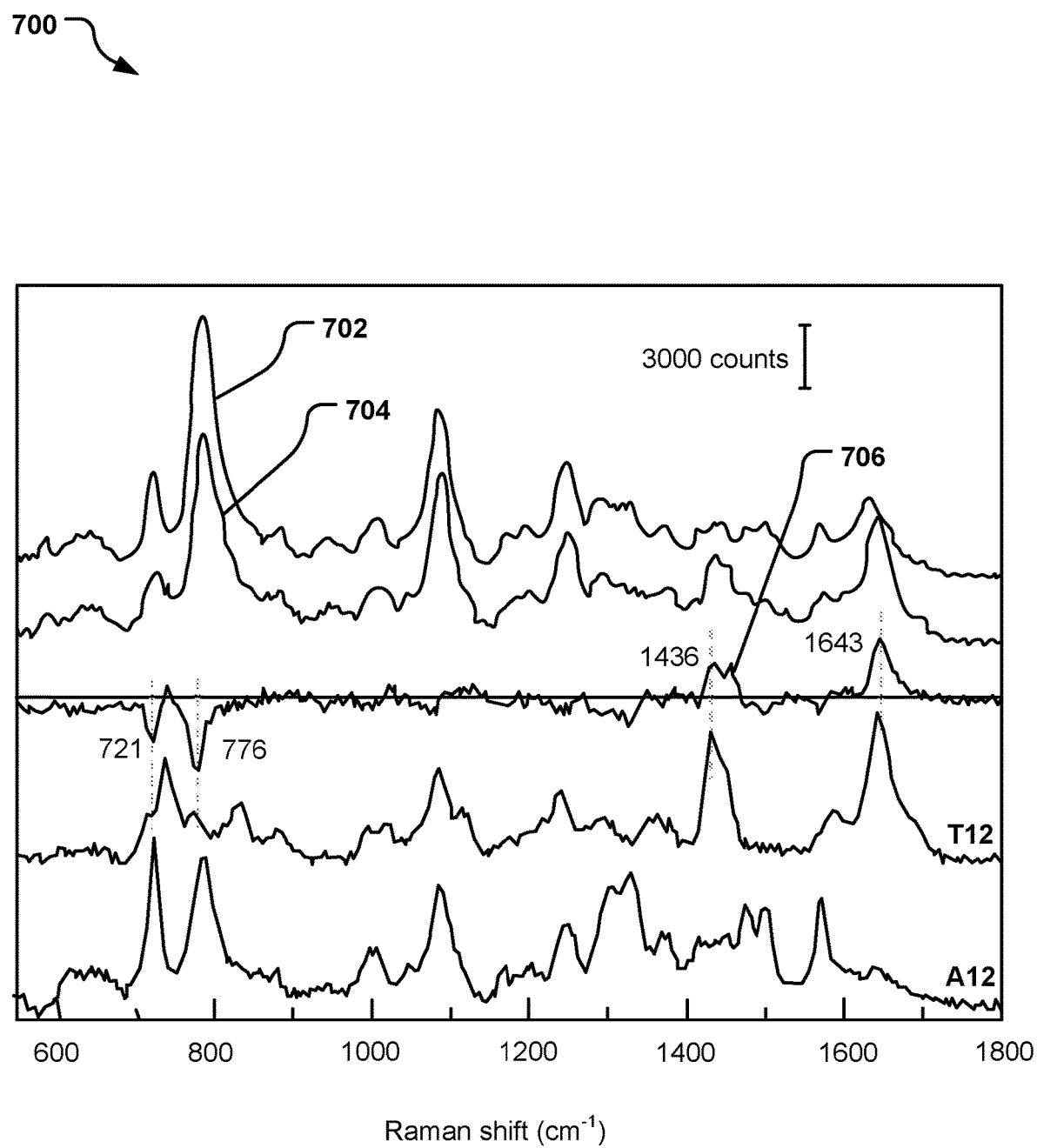
FIG. 7 is a graphical representation of SER spectra for a group of nucleotides.

FIG. 7 shows a SER spectra graph 700 of several example sequences. A first ten-nucleotide strand is shown as 702, the nucleotides being (ACA ACC CCC A). A second ten-nucleotide strand is shown as 704, the nucleotides being (TCA ACC CCC A), only one different from the first strand 702. A third line 706 represents the difference of the spectrum of the strand 702 and the strand 704. The difference in intensities at 721 $cm^{-1}$, 776 $cm^{-1}$, 1436 $cm^{-1}$ and 1643 $cm^{-1}$ are marked, and directly correspond to the frequencies expected for the substituted nucleotide, in this example, T for A, showing an increase at 1643 $cm^{-1}$ due to the presence of T, and a decrease at 776 $cm^{-1}$ due to the loss of A.

Also shown in FIG. 7 are spectra of T12 (i.e., a DNA sequence of 12 Ts) and A12 (i.e., a DNA sequence of 12 As) for a better identification of the peaks.

It is noted that each nucleotide will be observed twice: once as it enters the hot spot, and once as it exits the hot spot; such a double measurement improves accuracy. In addition, double measurement alleviates the detection difficulty that could arise when the identity of the exiting nucleotide happens to be the same as that of the entering nucleotide and the peak amplitudes do not change. In such cases, signal processing can take into account the turnover rate and the subsequent amplitude changes in order to identify the nucleotides in question.

In order to further improve accuracy, several SERS hot spots may be set up in series in a system, so that each nucleotide passes through several hot spots. FIG. 6 illustrates a sensor 600 having several SERS hot spots in series to enable multiple detections of each nucleotide for improved accuracy.

Figure 8:
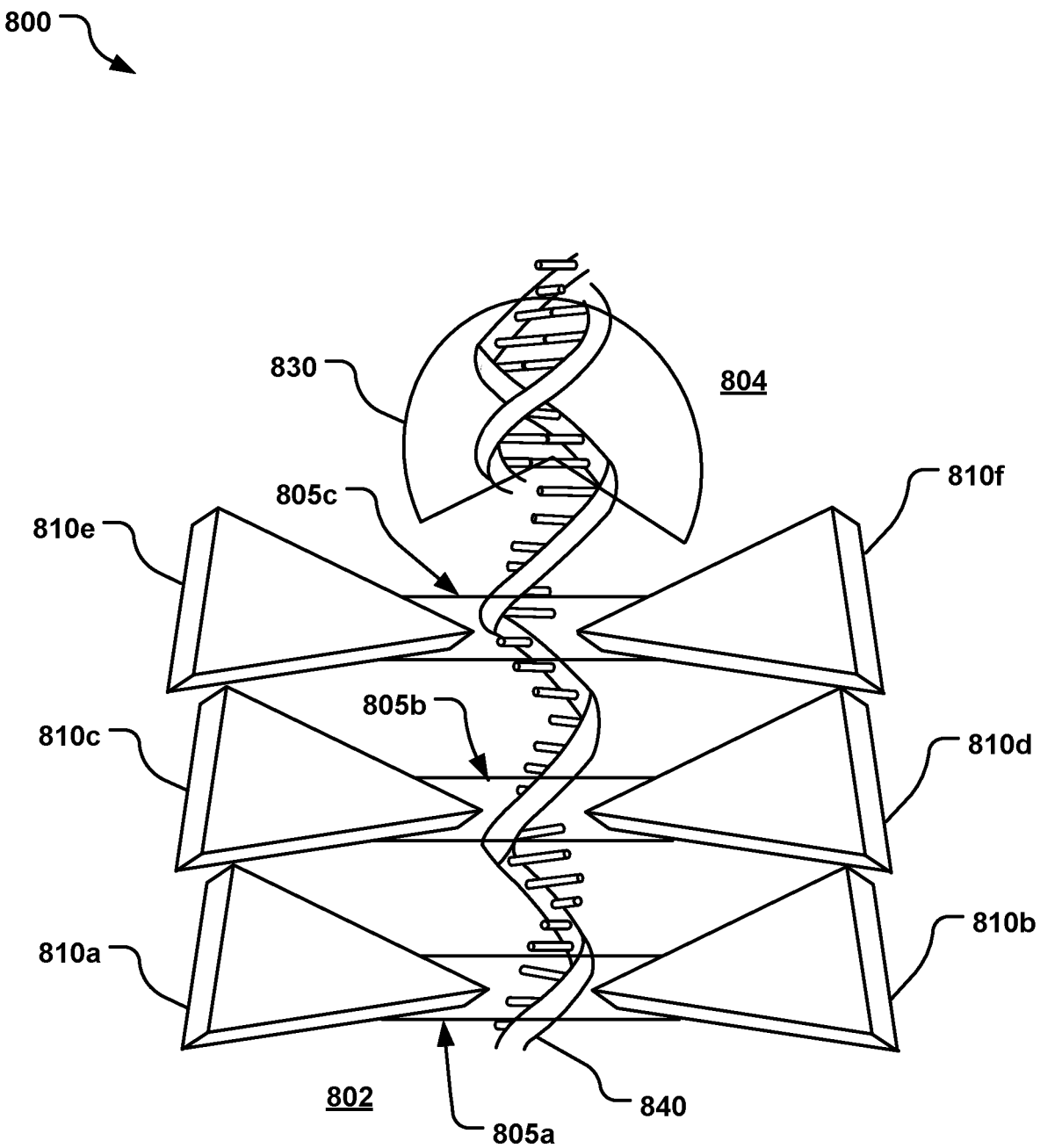
FIG. 8 is a schematic diagram of an alternate Raman sensor set-up.

In FIG. 8, the SERS sensor 6800 is schematically illustrated, almost in a cartoon manner. Again, only certain features of the sensor 80 are shown in FIG. 8; it is to be understood that the sensor 800 includes other features (e.g., laser(s)) as described in relation to FIG. 2.

The sensor 800 has a sample loading chamber 802, a secondary chamber 804, and at least one nanochannel hot spot 805 therebetween, particularly, three hot spots 805a, 805b, 805c arranged in series. Each nanochannel hot spot 805 is generated by laser excitation and enhanced by resonance of metallic (e.g., gold) nanostructures 810. In this particular implementation, three pairs of nanostructures 810 are illustrated as pair of nanostructures 810a, 810b, pair of nanostructures 810c, 810d, and pair of nanostructures 810e, 810f. The three pairs of nanostructures 810 are located along a length of a nanochannel, so that the nanochannel defines the distinction between the two chambers 802, 804. The sample loading chamber 802 is upstream of the nanochannel and the hot spots 805 and the secondary chamber 804 is downstream of the nanochannel and the hot spots 805.

A DNA polymerase 830 (illustrated as a Pac Man™ type shape) replicates a DNA template strand 840 to be sequenced. The DNA polymerase 830 may be immobilized, e.g., on a surface of the secondary chamber 804 or otherwise downstream of the nanochannel hot spots 805. The replicated complementary strand 850 is shown proximate the DNA polymerase 830. The action of replicating the template strand 840 by the DNA polymerase 830 applies a tension or force on the strand 840 and pulls the strand 840 through the hot spots 805.

As with the sensor 600, as the template strand 840 is pulled through the nanochannel and the hot spots 805 from the sample loading chamber 802 into the secondary chamber 804, a portion of the strand 840 is in each hot spot 805a, 805b, 805c. Each nucleotide in the template strand 840 will eventually pass through each of the multiple hot spots 805, thus ensuring multiple measurements of each nucleotide in the strand 840, improving accuracy.

Various additional and alternate implementations and designs are also contemplated.

In some implementations, the DNA template strand is a linear single strand (as shown, e.g., in FIG. 6 as template strand 640 or in FIG. 8 as template strand 840), whereas in other implementations the strand entering the hot spot is a double strand. A double strand is sequenced in the same manner as a single strand, other than the difference from one spectra measurement to the subsequent spectra measurement is two (complementary) nucleotides.

Either a single strand or double strand may contain an adapter sequence at one or both ends. Primers that are complementary to the adapter sequence(s) may be hybridized to a single template strand to create short double-stranded regions at one or both ends of the single template strand.

In another implementation, instead of using a DNA polymerase to pull the DNA strand through the hot spot(s), an exonuclease may be used. An immobilized exonuclease would pull the DNA strand through the nanochannel as it sequentially removes nucleotides one at a time. In an implementation using an exonuclease, no free nucleotides need be added to the secondary chamber, as with a polymerase.

In another implementation, an RNA polymerase or exonuclease may be used in place of a DNA polymerase or DNA exonuclease, in order to sequence RNA or DNA.

In some implementations, rather than using a DNA polymerase or exonuclease to pull the DNA strand through the hot spot(s), an electric current or voltage differential may be used to pull the strand through the hot spot(s) or aid in the pulling. Other sources of electrophoresis may additionally or alternatively be used, as well as another source of force, e.g., electromechanical.

A magnetic field may be used in some implementations to initiate and/or facilitate the DNA strand migration through the nanochannel. A magnetic bead may be attached to one end of the DNA strand so that it may respond to the applied magnetic field and be guided through the channel. It is noted that any such magnetic bead is not used for identification of the nucleotide or other component to which it is attached but is merely used as a transport facilitator.

As indicated above, the Raman-scattered photons may be filtered such that only photons of specific frequencies are detected. Such filtration may be performed with any number of ring resonators, waveguides, diffraction gratings, prisms, edge filters, notch filters, bandpass filters, directional couplers, MZI (Mach-Zehnder Interferometer) filters, AWG (Array waveguide gratings) etc.

Figure 9A:
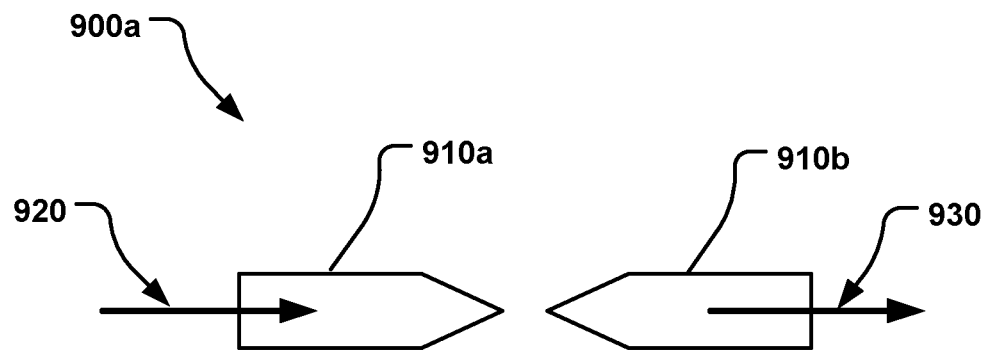
FIG. 9A is a schematic diagram of a system of nanostructures coupling to a detector in-plane.
Figure 9B:
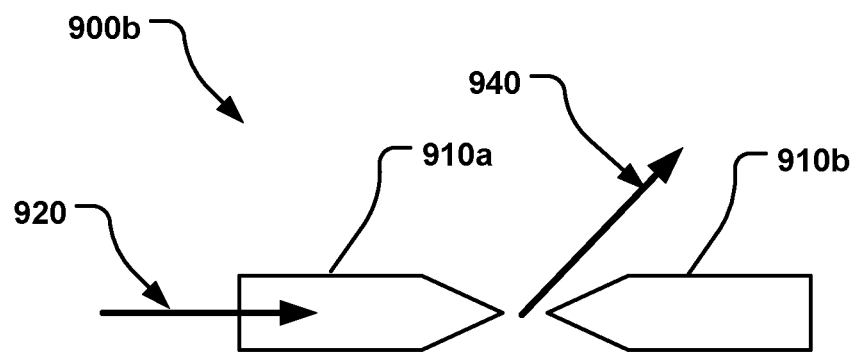
FIG. 9B is a schematic diagram of a system of nanostructures coupling to a detector out-of-plane.

FIGS. 9A and 9B show examples of detection orientation in relation to the nanostructures. In FIG. 9A, the sensor 900a has a first plasmonic nanostructure 910a and a second plasmonic nanostructure 910b. A source 920 and detector 930 are in the same plane (e.g., a guided light plane) and the nanostructures 910 and is orthogonal to the nanochannel between the nanostructures 910. In another implementation, the detector can be out-of-plane with respect to the plasmonic structure, as in FIG. 9B. In FIG. 9B, the sensor 900b has the source 920 in the same plane as the first plasmonic nanostructure 910a and the second plasmonic nanostructure 910b, however this detector 940 is out-of-the-plane of the nanostructures 910.

Figure 10A:
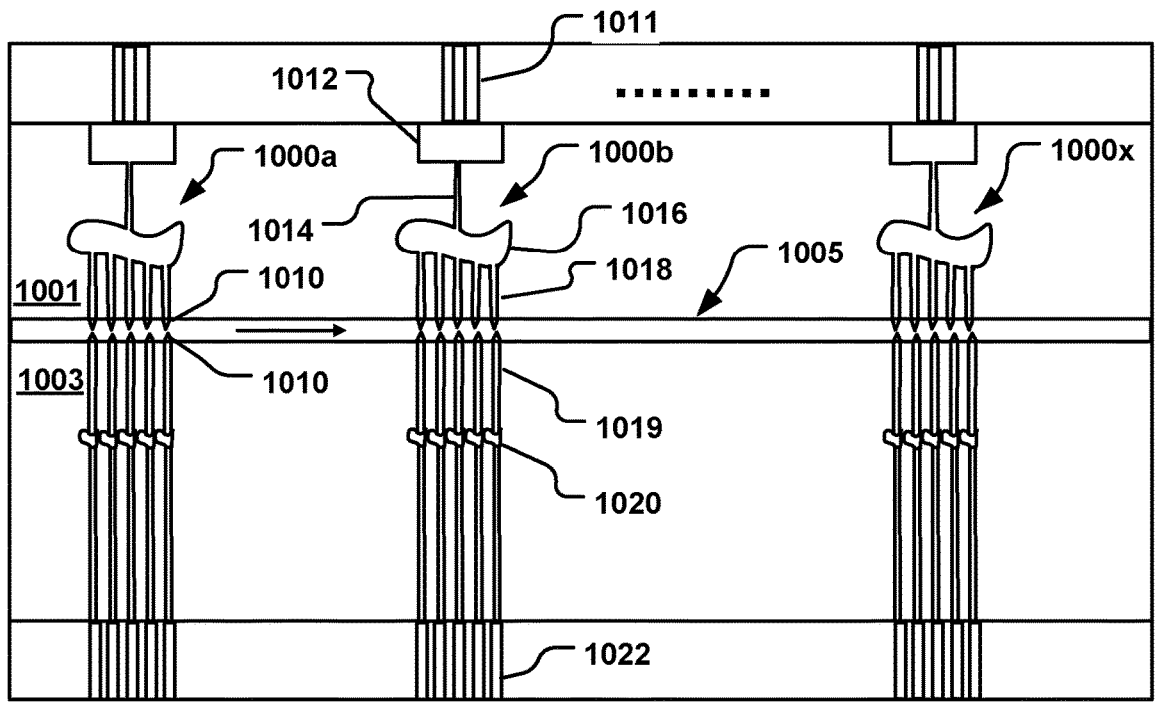
FIG. 10A is a schematic diagram of a system of sensors having plasmonic nanostructure excitation.
Figure 10B:
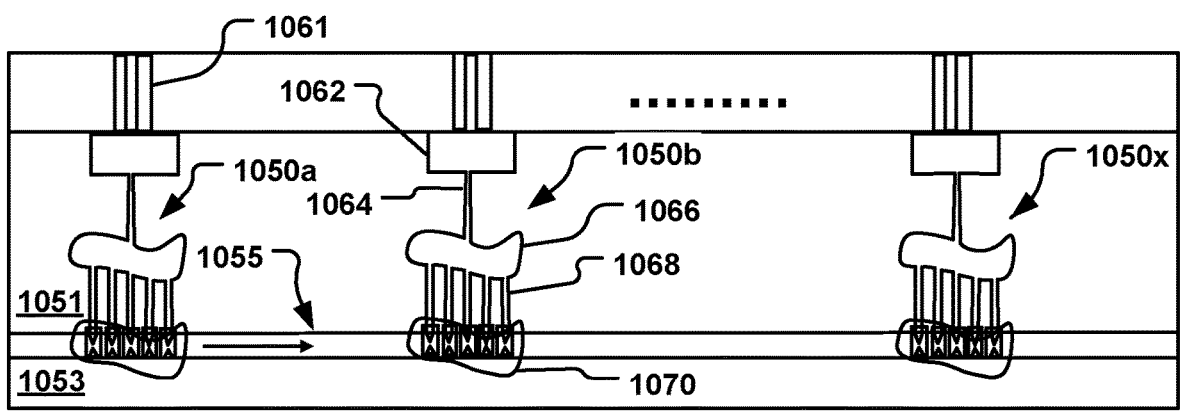
FIG. 10B is another schematic diagram of a system of sensors having plasmonic nanostructure excitation.

The sensors can be "on-chip; examples of on-chip implementations are shown in FIGS. 10A and 10B. FIG. 10A shows how a semiconductor laser can be used as source and light can be coupled to waveguide via coupler and filter to plasmonic nanostructures for exciting. The resulting Raman-scattered photons may be filtered such that only photons of specific frequencies are detected. Such filtration and detection could also be implemented in out-of-plane as shown in FIG. 10B.

In FIG. 10A, a system having a plurality of SERS sensors 1000 in series is shown. FIG. 10A shows at least three sensors 1000, sensor 1000a, sensor 1000b, . . . and sensor 1000x. The sensors 1000 have a first or input side 1001 and a second or output side 1003. A nanochannel 1005, through which a DNA strand to be sequenced passes, is present between the first side 1001 and the second side 1003. Each sensor 1000 has multiple nanostructures 1010 on the first side 1001 and the second side 1003.

In each sensor 1000, a coupler 1012 couples light from a laser 1011 (e.g., an on-chip laser) to a narrow waveguide 1014, then a spatial filter 1016 divides the optical power from one waveguide channel 1014 into multiple channels 1018, in this implementation into five channels 1018. All these channels 1018 then interact with the template DNA strand passing through the nanochannel 1005.

The Raman signal generated at the tip of the nanostructure 1010 is coupled to an outgoing waveguide 1019 that carries the signal to a filter 1020. Depending on the specific type of Raman signal, the filter 1020 guides the light to a specific detector 1022 or enables a specific response of the detector. Based on this detected Raman signal, as the DNA flows continuously, a specific pattern of DNA sequence, associated with the specimen is generated.

Similarly in FIG. 10B, a system is shown having a plurality of SERS sensors 1050 in series. FIG. 10B shows at least three sensors 1050, sensor 1050a, sensor 1050b, . . . and sensor 1050x. The sensors 1050 have a first or input side 1051 and a second or output side 1053. A nanochannel 1055, through which a DNA strand to be sequenced passes, is present between the first side 1051 and the second side 1053. Each sensor 1050 has multiple nanostructures (not called out in FIG. 10B) on the first side 1051 and the second side 1053.

In each sensor 1050, a coupler 1062 couples light from a laser 1061 (e.g., an on-chip laser) to a narrow waveguide 1064, then a spatial filter 1066 divides the optical power from one waveguide channel 1064 into multiple channels 1068, in this implementation into five channels 1068. All these channels 1068 then interact with the template DNA strand passing through the nanochannel 1055.

The Raman signal generated at the tip of the nanostructure is coupled to a filter layer 1070 on top of the nanochannel 1055. A detector layer (not seen) is present on top of the filter layer 1070. Depending on the specific type of Raman signal, the filter 1070 guides the light to a detector layer on top of the filter 1070. Based on this detected Raman signal, as the DNA flows continuously, a specific pattern of DNA sequence, associated with the specimen is generated.

Figure 11:
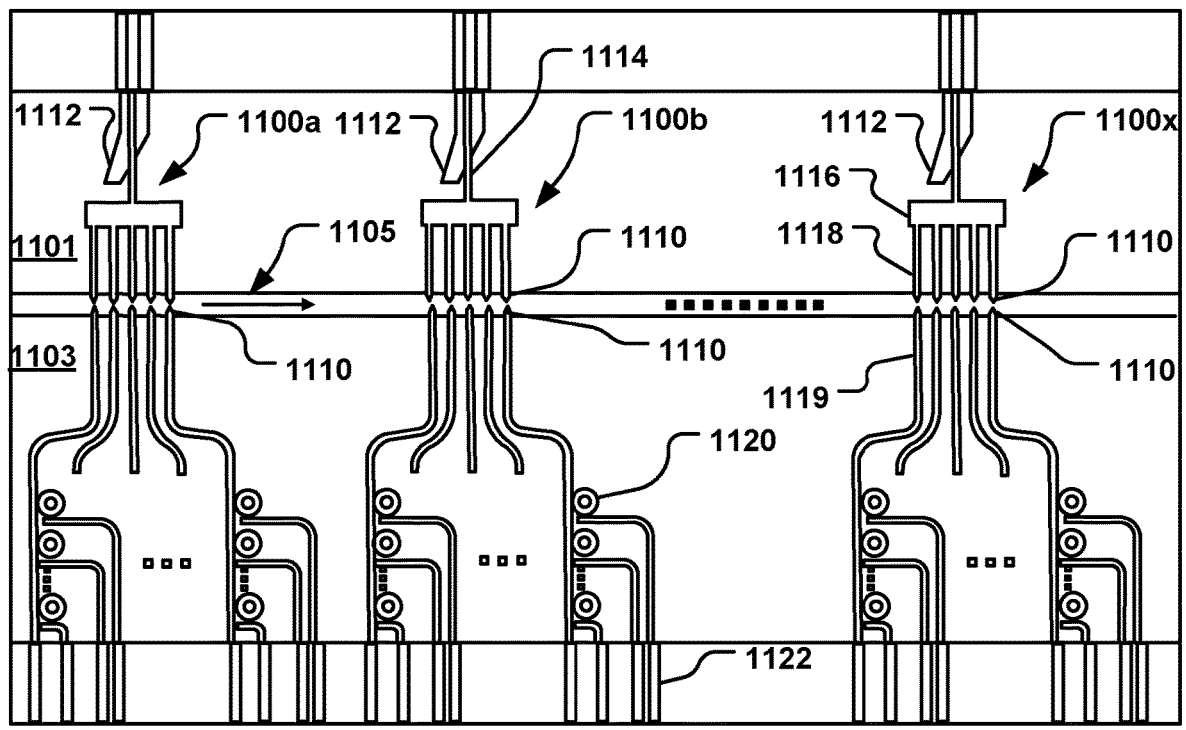
FIG. 11 is a schematic diagram of a system of sensors having multiple ring resonators to filter the output light.

Another and more specific example of an on-chip implementation is shown in FIG. 11, which shows a system having a plurality of SERS sensors 1100 in series, each with a knife coupler. FIG. 11 shows at least three sensors 1100, sensor 1100a, sensor 1100b, . . . and sensor 1100x (for example, x=200). The overall width of the system can be, e.g., 20 to 80 mm, depending on the number of sensors needed for the Raman shift. In each of the sensors 1100, only certain features of the sensor 1100 are shown in FIG. 11; it is to be understood that the sensor 1100 includes other features as described in relation to the sensors described above.

The sensors 1100 of FIG. 11 have a first or input side 1101 and a second or output side 1103. A nanochannel 1105, through which a DNA strand to be sequenced passes, is present between the first side 1101 and the second side 1103. Each sensor 1100 is shown with multiple nanostructures 1110 on the first side 1101 and the second side 1103.

In each sensor 1100, a knife coupler 1112 couples light from a laser (e.g., an on-chip laser) to a narrow waveguide 1114, then a spatial filter 1116 divides the optical power from one waveguide channel 1114 into multiple channels 1118, in this implementation into five channels 1118 All these channels 1118 then interact with the template DNA strand passing through the nanochannel 1105 via the plasmonic nanostructures 1110. Present in the channels 1118 may be, e.g., IBEX-like polarization rotators and/or arrow-like near-field transducers (NFTs).

The Raman signal generated at the tip of the nanostructure 1110 is coupled to an outgoing waveguide 1119 that carries the signal to a filter 1120, which may be any of a number of ring resonators, diffraction gratings, prisms, edge filters, notch filters, bandpass filters, directional couplers, MZI (Mach-Zehnder Interferometer) filters, AWG (Array waveguide gratings) etc. In FIG. 11, this filter 1120 is a ring resonator; the number of ring resonators is, e.g., 4 to 10, depending on the number of channels needed for the Raman shift.

Depending on the specific type of Raman signal, the filter 1120 guides the light to a specific detector 1122 or enables a specific response of the detector. Based on this detected Raman signal, as the DNA flows continuously, a specific pattern of DNA sequence, associated with the specimen is generated. The detectors may be, e.g., silicon photodetectors; the number of detectors is, e.g., 4,000 to 10,000, depending on the number of channels needed for the Raman shift.

In summary, described herein are methods of utilizing SERS to identify individual nucleotides of a DNA strand (e.g., a template strand) or of an RNA strand using a Raman sensor with focusing plasmonic nanostructures that create a hot spot. The sensor can include an immobilized DNA polymerase, which replicates the template strand being sequenced. The replication action by the polymerase pulls the strand through the Raman hot spot generated by laser excitation and enhanced by resonance due to the nanostructures.

The above specification and examples provide a complete description of the structure and use of exemplary implementations of the invention. The above description provides specific implementations. It is to be understood that other implementations are contemplated and may be made without departing from the scope or spirit of the present disclosure. The above detailed description, therefore, is not to be taken in a limiting sense. While the present disclosure is not so limited, an appreciation of various aspects of the disclosure will be gained through a discussion of the examples provided.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

Spatially related terms, including but not limited to, "bottom," "lower", "top", "upper", "beneath", "below", "above", "on top". "on," etc., if used herein, are utilized for ease of description to describe spatial relationships of an element(s) to another. Such spatially related terms encompass different orientations of the device in addition to the particular orientations depicted in the figures and described herein. For example, if a structure depicted in the figures is turned over or flipped over, portions previously described as below or beneath other elements would then be above or over those other elements.

Since many implementations of the invention can be made without departing from the spirit and scope of the invention, the invention resides in the claims hereinafter appended. Furthermore, structural features of the different implementations may be combined in yet another implementation without departing from the disclosure or the recited claims.

What is claimed is:

1. A method of sequencing a DNA strand, comprising:
   passing the DNA strand through a nanochannel hot spot of a Raman sensor bounded by plasmonic nanostructures and excited by at least one laser;
   identifying the nucleotides of a first section of the DNA strand present in the nanochannel at a first period in time by a Raman signature, and identifying the nucleotides of a second section of the DNA strand present in the nanochannel at a second period in time by a second Raman signature; and
   comparing the identified nucleotides of the first section to the identified nucleotides of the second section to identify a change.

2. The method of claim 1, wherein passing the DNA strand comprises passing a DNA template strand.

3. The method of claim 2, wherein passing the DNA template strand comprises pulling the DNA template strand via a DNA polymerase.

4. The method of claim 3, wherein pulling the DNA template strand via the DNA polymerase includes building a complementary strand from a plurality of individual free nucleotides.

5. The method of claim 1 wherein passing the DNA strand comprises pulling the DNA strand via a DNA exonuclease.

6. The method of claim 1 further comprising moving the template DNA strand to the nanochannel by electrophoresis or magnetophoresis.

7. The method of claim 1, where passing the DNA strand comprises passing the DNA strand through the nanochannel hot spot of a Raman sensor bounded by two gold plasmonic nanostructures, each excited by a laser.

8. A method of sequencing a DNA strand, comprising:
   passing the DNA strand through a nanochannel hot spot of a Raman sensor bounded by plasmonic nanostructures and excited by at least one laser;
   identifying a Raman signature of at least one nucleotide of a first section of the DNA strand present in the nanochannel at a first period in time, and identifying a second Raman signature of at least one nucleotide of a second section of the DNA strand present in the nanochannel at a second period;
   comparing the Raman signature of the first section to the second Raman signature of the second section to identify a change in the Raman signature; and
   correlating the change in the Raman signature to a single nucleotide.

9. The method of claim 8, wherein passing the DNA strand comprises passing a DNA template strand.

10. The method of claim 9, wherein passing the DNA template strand comprises pulling the DNA template strand via a DNA polymerase.

11. The method of claim 10, wherein pulling the DNA template strand via the DNA polymerase includes building a complementary strand from a plurality of individual free nucleotides.

12. The method of claim 8 wherein passing the DNA strand comprises pulling the DNA strand via a DNA exonuclease.

13. The method of claim 8 further comprising moving the template DNA strand to the nanochannel by electrophoresis or magnetophoresis.

14. The method of claim 8, where passing the DNA strand comprises passing the DNA strand through a nanochannel hot spot of a Raman sensor bounded by two gold plasmonic nanostructures, each excited by a laser.

15. A Surface-Enhanced Raman Spectroscopy (SERS) sensor comprising:
 a sample loading channel for receiving a DNA strand to be sequenced;
 a secondary chamber having an immobilized DNA polymerase therein;
 a nanochannel fluidly connecting the sample loading chamber and the secondary chamber;
 a SERS hot spot within the nanochannel downstream of the sample loading chamber and defined by at least two plasmonic nanostructures each having a laser focused thereon, the SERS hot spot sized to receive the DNA strand therethrough;
 a Raman detector operably connected to the SERS hot spot to measure Raman spectra from nucleotides of the DNA strand; and
 the secondary chamber downstream of the SERS hot spot.

16. The SERS sensor of claim 15, wherein the sample loading chamber is for receiving a DNA template strand to be sequenced.

17. The SERS sensor of claim 15, further comprising at least one light filter operably connected to the Raman detector.

18. The SERS sensor of claim 15, comprising four plasmonic nanostructures, the four plasmonic nanostructures arranged as two pairs.

19. The SERS sensor of claim 18, wherein a first pair of plasmonic nanostructures is upstream of a second pair of plasmonic nanostructures, with each pair of plasmonic nanostructures having a laser focused thereon defining a SERS hot spot.

20. The SERS sensor of claim 15 further comprising a waveguide optically connected to each of the at least two plasmonic nanostructures.

* * * * *